United States Patent
Nozawa et al.

(10) Patent No.: US 9,970,885 B2
(45) Date of Patent: May 15, 2018

(54) INSPECTION APPARATUS AND INSPECTION METHOD

(71) Applicant: Lasertec Corporation, Yokohama (JP)

(72) Inventors: Hiroto Nozawa, Kanagawa (JP); Kuniaki Takeda, Yokohama (JP); Kenshi Ishiwatari, Yokohama (JP); Takamasa Tsubouchi, Yokohama (JP); Ryoichiro Satoh, Yokohama (JP)

(73) Assignee: Lasertec Corporation, Yokohama (JP)

( * ) Notice: Subject to any disclaimer, the term of this patent is extended or adjusted under 35 U.S.C. 154(b) by 600 days.

(21) Appl. No.: 14/549,625

(22) Filed: Nov. 21, 2014

(65) Prior Publication Data

US 2015/0144769 A1 May 28, 2015

(30) Foreign Application Priority Data

Nov. 26, 2013 (JP) ................ 2013-243704

(51) Int. Cl.
*G01N 21/00* (2006.01)
*H01L 21/00* (2006.01)
(Continued)

(52) U.S. Cl.
CPC .......... *G01N 21/8851* (2013.01); *G06T 5/50* (2013.01); *G06T 7/0004* (2013.01);
(Continued)

(58) Field of Classification Search
None
See application file for complete search history.

(56) References Cited

U.S. PATENT DOCUMENTS

| 5,640,237 A | 6/1997 | Esrig et al. |
| 2002/0093647 A1 | 7/2002 | Fukazawa et al. |

(Continued)

FOREIGN PATENT DOCUMENTS

| JP | 09-178663 | 11/1997 |
| JP | 2001041720 | 2/2001 |

(Continued)

OTHER PUBLICATIONS

Sasaki et al; An In-line Image Quality Monitoring System for Imaging Device Fabrication using Automated Macro-Inspection; System Solution Tech Development No. 1; IBM Japan.

(Continued)

*Primary Examiner* — Renee Chavez
(74) *Attorney, Agent, or Firm* — Faegre Baker Daniels LLP

(57) ABSTRACT

An inspection apparatus and an inspection method capable of performing an inspection more accurately are provided. An inspection apparatus according to the present invention includes a light source 10 that illuminates a sample 30 in which a pattern is formed, a detector 11 that detects light reflected from the sample 30 illuminated by the light source, and a processing device 50 that performs an inspection based on a correlation between a brightness value of a sample image obtained by the detector and a size in a surface shape or a size in a width direction of the pattern of the sample 30. The processing device 50 performs the inspection based on a summation value obtained by adding up brightness values of sample images with weights, the sample images being obtained under a plurality of shooting conditions.

14 Claims, 4 Drawing Sheets

(51) Int. Cl.
  *G01B 11/00* (2006.01)
  *G01N 21/88* (2006.01)
  *G06T 7/00* (2017.01)
  *G06T 5/50* (2006.01)
  *G01N 21/95* (2006.01)
  *G01N 21/956* (2006.01)

(52) U.S. Cl.
  CPC . *G01N 21/9501* (2013.01); *G01N 2021/8845* (2013.01); *G01N 2021/8848* (2013.01); *G01N 2021/9513* (2013.01); *G01N 2021/95676* (2013.01); *G06T 2207/10152* (2013.01); *G06T 2207/30148* (2013.01)

(56) References Cited

U.S. PATENT DOCUMENTS

| | | | |
|---|---|---|---|
| 2003/0057384 | A1 | 3/2003 | Fukazawa |
| 2008/0049214 | A1* | 2/2008 | Maznev ............... G01B 11/22 356/51 |
| 2010/0295941 | A1* | 11/2010 | Jeong ............... G01B 11/2531 348/135 |
| 2011/0188779 | A1 | 8/2011 | Sakanaga et al. |
| 2015/0168303 | A1* | 6/2015 | Trupke ............... G01N 21/6456 324/762.01 |

FOREIGN PATENT DOCUMENTS

| | | |
|---|---|---|
| JP | 2002162367 | 6/2002 |
| JP | 2002162368 | 6/2002 |
| JP | 2004-093338 A | 3/2004 |
| JP | 2007327796 | 12/2007 |
| JP | 200931212 | 2/2009 |
| JP | 2011-163766 A | 8/2011 |
| JP | 2012103052 | 5/2012 |
| JP | 2013174575 | 5/2013 |
| JP | 2013108779 | 6/2013 |

OTHER PUBLICATIONS

Markwort et al; Full wafer macro-CD imaging for excursion control of fast patterning processes; Metrology, Inspection, and Process Control for Microlithography XXIV; 2010.
Office Action dated Aug. 12, 2014 on patent application JP2013-250891.
Office Action dated May 12, 2015 in the corresponding JP Patent Application (Japanese Document and English translation attached).
Office Action dated Dec. 16, 2014 on patent application JP2013-243704.

* cited by examiner

ION APPARATUS AND INSPECTION METHOD

INCORPORATION BY REFERENCE

This application is based upon and claims the benefit of priority from Japanese patent application No. 2013-243704, filed on Nov. 26, 2013, the disclosure of which is incorporated herein in its entirety by reference.

BACKGROUND OF THE INVENTION

1. Field of the Invention

The present invention relates to an inspection apparatus and an inspection method.

2. Description of Related Art

As a technique for swiftly inspecting a surface of a semiconductor wafer or the like, a macro inspection apparatus has been used (Non-patent literature 1 and 2). Since a macro inspection apparatus takes an image of a wafer at a low magnification, it can inspect the whole wafer in a short time. For example, the macro inspection apparatus disclosed in Non-patent literature 1 takes an image of a wafer by illuminating the wafer in an oblique direction. The intensity of the reflected light changes as the line width of a pattern (line width) changes. Therefore, linearity between line widths and brightness values is obtained in Non-patent literature 1.

[Non-Patent Literature 1] An In-line Image Quality Monitoring System for Imaging Device Fabrication using Automated Macro-Inspection, Tohru Sasaki et al., Proc. SPIE 6152, Metrology, Inspection, and Process Control for Microlithography XX, 61522W (Mar. 24, 2006)

[Non-Patent Literature 2] Full wafer macro-CD imaging for excursion control of fast pattering process, Lars Markwort et al., Proc. SPIE 7638, Metrology, Inspection, and Process Control for Microlithography XXIV, 763807 (Apr. 1, 2010)

In a macro inspection apparatus, an inspection is performed by associating intensities of received light (brightness values) of a detector with CD values. For example, in FIG. 1 of Non-patent literature 1, the brightness value increases as the pattern width becomes wider. In other words, a brightness distribution corresponds to a CD distribution, thus making it possible to perform a CD inspection based on the brightness distribution.

Regarding the above-described inspection apparatus, it is desired to perform an inspection more accurately. However, the brightness value in the detector changes depending on the pattern and the film-thickness of a base layer and the like as well as depending on the CD value. That is, the brightness value includes information of the film-thickness and the like in addition to the CD value. Further, it also includes changes of the brightness value caused by shading and the like of the optical system. As a result, in Non-patent literature 1, there is a possibility of occurrences of an error due to the association between the CD values and the brightness values could increase. Consequently, there is a problem that it is very difficult to accurately perform an inspection in the above-described method.

The present invention has been made in view of the above-described circumstances, and an object thereof is to provide an inspection apparatus and an inspection method capable of performing an inspection more accurately.

SUMMARY OF THE INVENTION

A first exemplary aspect of the present invention is an inspection apparatus including: a light source that illuminates a sample on which a pattern is formed; a detector that detects light reflected from the sample illuminated by the light source; and a processing device that performs an inspection based on a correlation between a brightness value of a sample image obtained by the detector and a size in a surface shape or a size in a height direction of the pattern of the sample, in which the processing device performs the inspection based on a summation value obtained by adding up brightness values of sample images with weights, the sample images being obtained under a plurality of shooting conditions. This configuration makes it possible to perform an accurate inspection.

In the above-described inspection apparatus, parameters for the addition with weights may be calculated based on a measured value of the size obtained by measuring a reference sample and a brightness value of a sample image of the reference sample by using a statistical technique. This makes it possible to use appropriate parameters and thereby to perform an inspection more accurately.

In the above-described inspection apparatus, a multiple regression analysis may be used as the statistical technique. This makes it possible to use parameters that reduce an error and thereby to perform a highly accurate inspection.

In the above-described inspection apparatus, the shooting condition may be changed by changing at least one of a wavelength of illumination light, polarization of the illumination light, an illuminating angle of the illumination light, a shape of the illumination light, a detecting angle of the detector, and an angle of the sample. This makes it possible to easily set appropriate shooting conditions.

In the above-described inspection apparatus, when at least one of a size of the surface shape and a size in the height direction of the pattern is an item to be inspected, shooting conditions whose sensitivities for an item other than the item to be inspected are equivalent to each other are preferably set. This makes it possible to appropriately extract information of the item to be inspected and thereby to perform an inspection with the appropriate information.

In the above-described inspection apparatus, the sample may be a semiconductor wafer, a TFT substrate, or a photomask, and a CD of the pattern, a film thickness, a taper angle, or a surface profile may be inspected. This makes it possible to accurately inspect the CD value of the pattern, the film thickness, the taper angle, or the surface profile.

Another exemplary aspect of the present invention is an inspection method including: illuminating a sample on which a pattern is formed; detecting light reflected from the sample illuminated; and performing an inspection based on a correlation between a brightness value of a sample image obtained and a size in a surface shape or a size in a height direction of the pattern of the sample, in which the inspection is performed based on a summation value obtained by adding up brightness values of sample images with weights, the sample images being obtained under a plurality of shooting conditions.

In the above-described inspection method, parameters of the addition with weights may be calculated based on a measured value of the size obtained by measuring a reference sample and a brightness value of a sample image of the reference sample by using a statistical technique. This makes it possible to use appropriate parameters and thereby to perform an inspection more accurately.

In the above-described inspection method, a multiple regression analysis may be used as the statistical technique. This makes it possible to use parameters that reduce an error and thereby to perform a highly accurate inspection.

In the above-described inspection method, the shooting condition may be changed by changing at least one of a wavelength of illumination light, polarization of the illumination light, an illuminating angle of the illumination light, a shape of the illumination light, a detecting angle of the detector, and an angle of the sample. This makes it possible to easily set an appropriate shooting condition.

In the above-described inspection method, when at least one of a size of the surface shape and a size in the height direction of the pattern is chosen as an item to be inspected, shooting conditions whose sensitivities for an item other than the item to be inspected are substantially equal to each other are preferably set. This makes it possible to appropriately extract information of the item to be inspected and thereby to perform an inspection with the appropriate information.

In the above-described inspection method, the sample may be a semiconductor wafer, a TFT substrate, or a photomask, and a CD value of the pattern, a film thickness, a taper angle, or a surface profile may be inspected. This makes it possible to accurately inspect the CD value of the pattern, the film thickness, the taper angle, or the surface profile.

According to the present invention, an inspection apparatus and an inspection method capable of performing an inspection more accurately can be provided.

The above and other objects, features and advantages of the present invention will become more fully understood from the detailed description given hereinbelow and the accompanying drawings which are given by way of illustration only, and thus are not to be considered as limiting the present invention.

DESCRIPTION OF THE EXEMPLARY EMBODIMENTS

Exemplary embodiments according to the present invention are explained hereinafter with reference to the drawings. The following explanations are given just to show preferred exemplary embodiments according to the present invention, and the scope of the present invention should not be limited to the below-shown exemplary embodiments. In the following explanations, components/structures to which the same symbols are assigned are substantially equivalent to each other.

An inspection apparatus according to this exemplary embodiment is a macro inspection apparatus that inspects a sample such as a semiconductor wafer on which a fine pattern is formed. The inspection apparatus performs a macro inspection based on brightness values of sample images. For example, the inspection apparatus inspects a pattern that is formed by liquid immersion exposure, EUV (Extreme Ultra Violet) exposure, or the like. The sample may be a semiconductor wafer for a NAND-type flash memory, a DRAM (Dynamic Random Access Memory), an SRAM (Static Random Access Memory), or the like, on which a periodic pattern is formed. The inspection apparatus takes images of the sample on which a pattern is periodically formed, and detects a line width (CD) distribution of the pattern, a film-thickness distribution, a taper angle distribution, and/or a surface profile. Alternatively, the inspection apparatus may inspect a patterned substrate for a liquid crystal display panel such as a TFT (Thin film transistor) substrate, or a photomask instead of the semiconductor wafer. As an example, a case where a semiconductor wafer is inspected is explained hereinafter.

Figure 1:
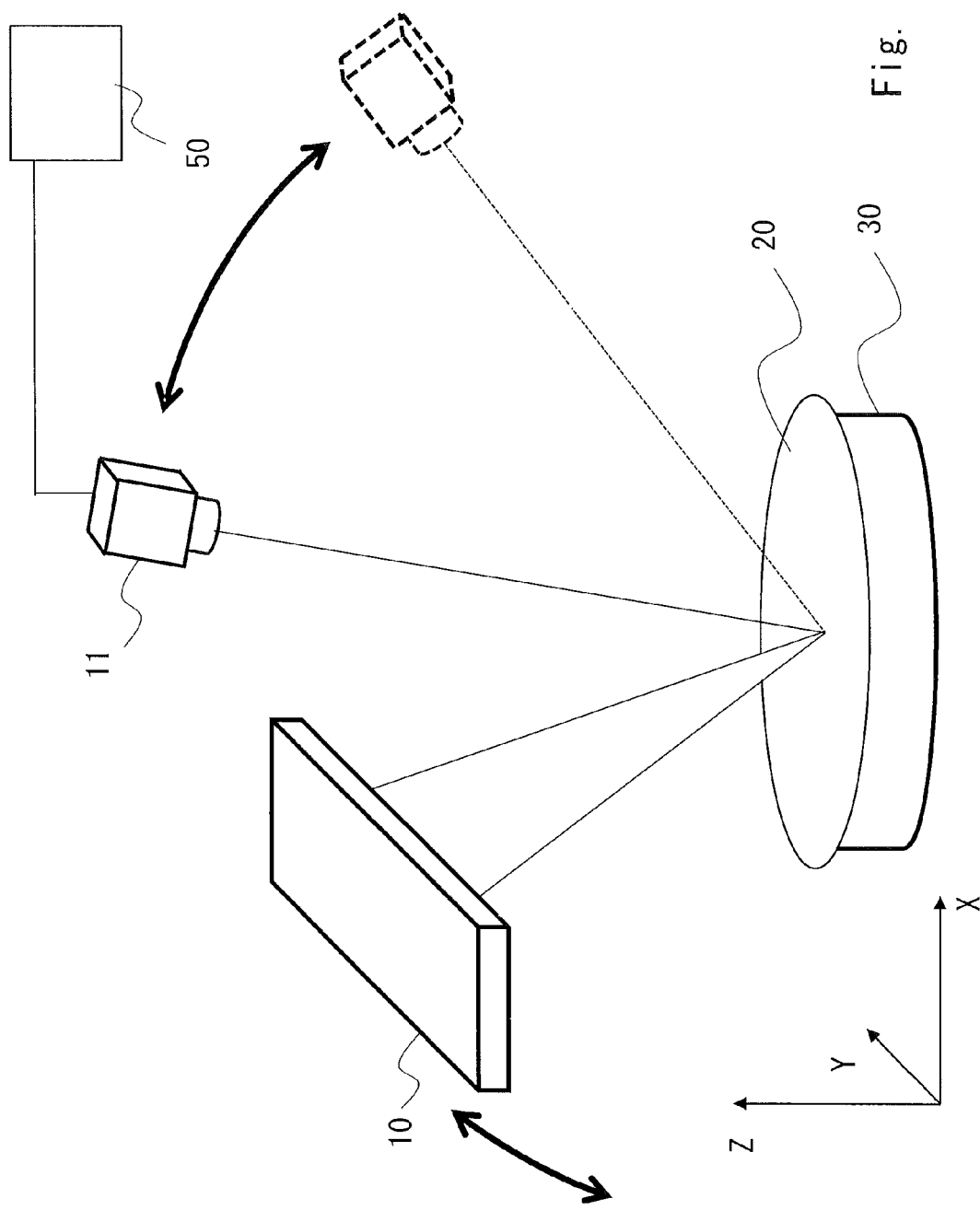
FIG. 1 shows an overall configuration of an inspection apparatus according to an exemplary embodiment.

A configuration of an inspection apparatus according to this exemplary embodiment is explained with reference to FIG. 1. FIG. 1 is a perspective view showing an overall configuration of the inspection apparatus. The inspection apparatus includes a light source 10, a detector 11, a stage 30, and a processing device 50. Further, FIG. 1 shows a three-dimensional orthogonal coordinate system consisting of XYZ-axes for clarifying the explanation. Note that the Z-direction is the vertical direction, and is a direction perpendicular to the pattern formation surface of a sample 20. The X- and Y-directions are horizontal directions, and are directions in parallel with the pattern formation surface of the sample 20.

The light source 10 and the detector 11 are disposed above the sample 20. The light source 10 is, for example, a linear light source that emits illumination light having a linear shape. Alternatively, the light source 10 may emit illumination light having a ring shape or a planar shape. The light source 10 emits, for example, illumination light such as visible light or infrared light. The light source 10 illuminates the sample 20 in an oblique direction, i.e., in a direction inclined from the Z-axis. Alternatively, the light source 10 illuminates the sample 20 from a position located on the Z-axis. The illumination light uniformly illuminates a linear shape area along the Y-direction on the surface of the sample 20. On the surface of the sample 20, the length of the illumination light along the Y-direction extends over the entire inspection area of the sample 20.

The illumination light emitted from the light source 10 illuminates a linear shape area on the surface of the sample 20. Then, light reflected in the illuminated linear shape area is detected by the detector 11. The detector 11 may be a line sensor camera in which light-receiving pixels are arranged in a row in the Y-direction. Therefore, since the intensity of the reflected light changes according to the surface state of the sample 20, the pattern size, and the like, the brightness value in the detector 11 changes.

The pixel size of the detector 11 is, for example, in the order of several μm to several tens of μm. Further, the pixel size on the sample 20 is roughly the same as that of the detector 11. Note that a line sensor in which photodiodes are arranged in a row can be used as the detector 11. The detector 11 and the light source 10 are obliquely disposed with respect to the Z-direction. The pattern size on the sample 20 is sufficiently smaller than the pixel size on the sample 20. Note that the illuminating angle of the illumination light emitted from the light source 10 on the XZ-plane may be equal to the angle of the detector 11, or may be different from the angle of the detector 11.

Further, the respective angles of the light source 10 and the detector 11 are changeable. For example, the illuminating angle of the illumination light can be changed by rotating the light source 10 around the Y-axis. Further, the detecting angle of detector 11 can be changed by rotating the detector 11 around the Y-axis. The respective angles of the light source 10 and the detector 11 can be adjusted independently of each other. Alternatively, the respective angles of the illumination light and the detector 11 may be changed by tilting the stage 30 around the X- or Y-axis.

The sample 20, which is the object to be inspected, is placed on the stage 30. The sample 20 is a patterned substrate such as a mask or a semiconductor wafer. The surface of the sample 20 is perpendicular to the Z-direction. Further, the stage 30 can be moved in the X-direction. The detector 11 detects light reflected in the area illuminated by the light source 10 while the stage 30 is being moved in the X-direction. Then, detection data according to the brightness of the light detected by the detector 11 is input to the processing device 50. Further, the processing device 50 controls the driving of the stage 30. Then, the processing device 50 visualizes the brightness changes of the light detected by the detector 11. In this way, a reflection image of the entire surface of the sample 20 can be obtained.

Further, the stage 30 can rotate around the Z-axis. By doing so, the angle of the sample 20 on the XY-plane can be changed. That is, the angle of the pattern with respect to the illumination light can be changed.

The light source 10 simultaneously illuminates the entire length of the sample 20 in the Y-direction. That is, an optical system having a low magnification and a wide field of vision is used. In this way, since an inspection can be performed with a high throughput by using an optical system having a low magnification, the inspection can be performed at a speed of 10 to 150 samples per hour. Since the throughput is high, every wafer can be inspected during the manufacturing process.

For example, the processing device 50 obtains images of a semiconductor wafer on which a pattern of a resist, lines, or the like is formed. The processing device 50 performs an inspection based on the obtained images. For example, when there are variations in the film-thickness or in the CD, the intensity of the reflected light changes. Consequently, the brightness of the sample images changes. Therefore, it is possible to inspect the variations in the film-thickness, in the CD, or the like based on the brightness changes of the sample images. An example case where variations in the CD are inspected is explained hereinafter.

In the following example, the processing device 50 is, for example, an information processing apparatus such as a personal computer, and performs processes for obtained sample images. The processing device 50 performs an inspection based on a correlation between the brightness values of sample images obtained by the detector 11 and the sizes of the pattern in the height direction or in the width direction of the sample 20. Specifically, the processing device 50 performs processes for carrying out a CD inspection. When an abnormality in the CD is detected by the CD inspection, the detection result is fed back to the manufacturing process and the like and a rework process or the like is performed based on the feedback. As a result, the productivity can be improved.

In order to perform a CD inspection, the detector 11 takes images of the sample 20 under different shooting conditions. That is, the inspection apparatus obtains sample images while changing the shooting condition. Then, in this exemplary embodiment, the processing device 50 converts brightness values of a plurality of sample images into a CD value(s). The processing device 50 inspects the sample 20 based on the plurality of sample images that are obtained under different shooting conditions.

Figure 2:
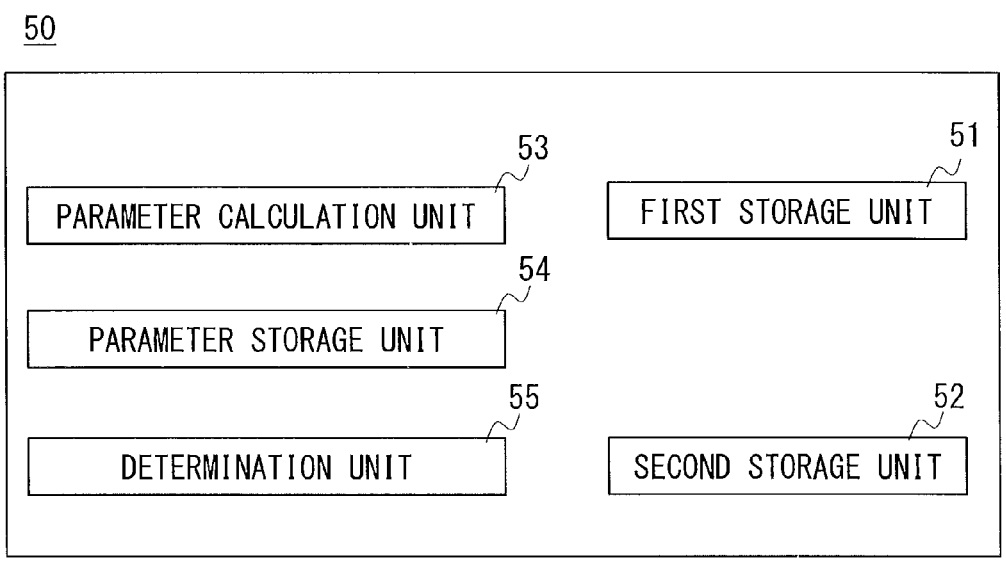
FIG. 2 is a block diagram showing a configuration of a processing device.

A configuration of the processing device 50 and processes performed thereby are explained with reference to FIG. 2. FIG. 2 is a block diagram showing a configuration of the processing device 50. The processing device 50 includes a first storage unit 51, a second storage unit 52, a parameter calculation unit 53, a parameter storage unit 54, and a determination unit 55.

The processing device 50 is a personal computer or the like and executes the following process. The units of the processing device 50 may each be configured, as hardware, by a CPU, memory, or a circuit in another form, or, as software, by a program loaded into a memory. Accordingly, these function blocks may be realized in a form of hardware, software, or a combination of the two as commonly understood by persons having ordinary skill in the art, and are not be limited to any specific form. Further, it is to be noted that the elements having substantially the same features depicted in the drawings will be assigned the same reference numerals, and the description thereof will not be repeated as appropriate.

Further, the program may be stored by using various types of non-transitory computer readable medium, and supplied to computers. The non-transitory computer readable medium includes various types of tangible storage medium. Examples of the non-transitory computer readable medium include a magnetic recording medium (such as a flexible disk, a magnetic tape, and a hard disk drive), a magneto-optic recording medium (such as a magneto-optic disk), a CD-ROM (Read Only Memory), a CD-R, and a CD-R/W, and a semiconductor memory (such as a mask ROM, a PROM (Programmable ROM), an EPROM (Erasable PROM), a flash ROM, and a RAM (Random Access Memory)). Further, the program may be supplied to computers by using various types of transitory computer readable media. Examples of the transitory computer readable media include an electrical signal, an optical signal, and an electromagnetic wave. The transitory computer readable media may be used to supply programs to computer through a wire communication path such as an electrical wire and an optical fiber, or wireless communication path.

As explained above, the inspection apparatus obtains sample images while changing the shooting condition. The first storage unit 51 stores image data detected by the detector 11. That is, the first storage unit 51 stores the brightness value of each pixel of the detector 11. The second storage unit 52 stores image data detected by the detector 11. That is, the second storage unit 52 stores the brightness value of each pixel of the detector 11. The sample image stored in the first storage unit 51 and that stored in the second storage unit 52 are taken under mutually different shooting conditions. In the following explanation, the sample image stored in the first storage unit 51 is referred to as "first sample image" and the sample image stored in the second storage unit 52 is referred to as "second sample image". That is, the sample image taken under a first shooting condition becomes the first sample image and the sample image taken under a second shooting condition becomes the second sample image.

Examples of the shooting conditions include the angle of the illumination light around the Y-axis, the angle of the detector 11 around the Y-axis, the angle of the sample 20 around the Z-axis, the wavelength of the illumination light, the polarization of the illumination light, and the spot shape of the illumination light on the sample 20. A plurality of sample images are obtained while changing at least one of the angle of the illumination light around the Y-axis, the angle of the detector 11 around the Y-axis, the angle of the sample 20 around the Z-axis, the wavelength of the illumination light, the polarization of the illumination light, and the spot shape of the illumination light. By doing so, appropriate shooting conditions can be easily selected.

When the angle of the illumination light around the Y-axis is changed, the light source 10 may be moved. When the angle of the detector 11 around the Y-axis is changed, the detector 11 may be moved. Alternatively, the stage 30 may be tilted in the Y-direction. When the angle of the sample 20 around the Z-axis is changed, the stage 30 may be rotated. Alternatively, the direction in which the sample 20 is placed on the stage 30 may be changed. When the wavelength of the illumination light is changed, a wavelength filter may be placed on the optical path. Then, the wavelength of the illumination light can be changed by changing the wavelength filter placed on the optical path. Alternatively, the wavelength of the illumination light may be changed by using a plurality of different light sources.

When the polarization state is changed, a polarizing plate may be placed on the optical path. For example, the polarization direction can be changed by rotating the polarizing plate by 90 degrees. When the spot shape of the illumination light is changed, the width of the line illumination, for example, may be changed. Alternatively, ring illumination may be used. When the ring illumination is used, the shooting condition may be changed by changing the size of the ring illumination. In this way, the shooting condition is changed so that the intensity of the light reflected on the sample 20 changes. Needless to say, the first and second sample images may be obtained while changing at least two of the above-listed shooting conditions at the same time.

The parameter calculation unit 53 calculates parameters for an addition with weights. A calculation method for the parameters for the addition with weights will be explained later. The parameter storage unit 54 stores the parameters calculated by the parameter calculation unit 53. The determination unit 55 performs an addition of the first and second sample images with weights using the parameters and thereby generates a summation image. In particular, the determination unit 55 calculates a summation value obtained by adding up brightness values with weights for each pixel. Since the position of the stage 30 is controlled by the processing device 50, a brightness value according to the XY-position on the sample 20 is detected. Alternatively, instead of adding up brightness values for each pixel, brightness values for each specified area may be added up. For example, average values of brightness values over a plurality of pixels may be added up with weights.

The determination unit 55 converts brightness values into a CD value(s) by adding up a plurality of sample images with weights. The determination unit 55 performs a pass/fail determination by comparing the brightness value of the summation image with a threshold. For example, the determination unit 55 determines whether or not the summation value of brightness values is within a normal range between upper and lower limit values. When the brightness value of the summation image is between the upper and lower limit values, the determination unit 55 determines that it is normal. On the other hand, when the brightness value of the summation image is higher the upper limit value or lower than lower limit value, the determination unit 55 determines that it is abnormal.

For example, brightness values are converted into a CD value(s) by performing an addition with weights in accordance with the below-shown Expression (1).

$$CD\ value = Image1 \times a1 + Image2 \times a2 + b \quad (1)$$

In the expression, Image1 is a brightness value of a first sample image and Image2 is a brightness value of a second sample image. Constants a1, a2 and b are parameters for an addition with weights. It is possible to associate brightness values of a plurality of sample images with a CD value(s) by using the parameters for the addition with weights.

The brightness value changes according to the CD value of the pattern on the sample 20. Similarly, the brightness value changes according to the film-thickness of the pattern on the sample 20. Therefore, the brightness value distribution of a sample image includes information about the CD distribution and the film-thickness distribution. That is, since the brightness value depends on the CD value and the film-thickness, the change of the brightness value due to the film-thickness change is added to the change of the brightness value due to the CD change. Further, the change of the brightness value due to shading and the like of the optical system is also added. Therefore, in the configuration in which the brightness value of only one sample image is compared with a threshold, when there is a brightness change, it is impossible or very difficult to determine whether the change is caused by variations in the CD, variations in the film-thickness, or shading of the optical system. As described above, in the related art method, it is very difficult to obtain information about only the item to be inspected.

Accordingly, this exemplary embodiment uses a plurality of sample images obtained under mutually different shooting conditions. For example, a plurality of shooting conditions having different sensitivities to the item to be inspected and the same sensitivity to an item(s) other than the item to be inspected are selected. That is, when the CD value is the item to be inspected, shooting conditions having different sensitivities to the CD value and the same sensitivity to the film-thickness and the like, i.e., an item(s) other than the item to be inspected (i.e., the CD value) are selected. As a result, it is possible to extract information about only the item to be inspected by performing an addition with weights for the selected plurality of shooting conditions. In this way, it is possible to associate the summation value with the CD value with high accuracy. Therefore, the CD inspection can be performed more accurately.

As an example of the above-described inspection procedure, the determination of the weighting parameters is made only when the inspection recipe is created. Then, the inspection time can be reduced by applying the above-described determined weighting parameters during the inspection that is performed after the inspection recipe is created.

Further, as described above, the shooting conditions such as the angle of the illumination light around the Y-axis, the angle of the detector 11 around the Y-axis, the angle of the sample 20 around the Z-axis, the wavelength of the illumination light, the polarization of the illumination light, and the spot shape of the illumination light are changed. In this way, appropriate shooting conditions can be easily set.

Figure 3:
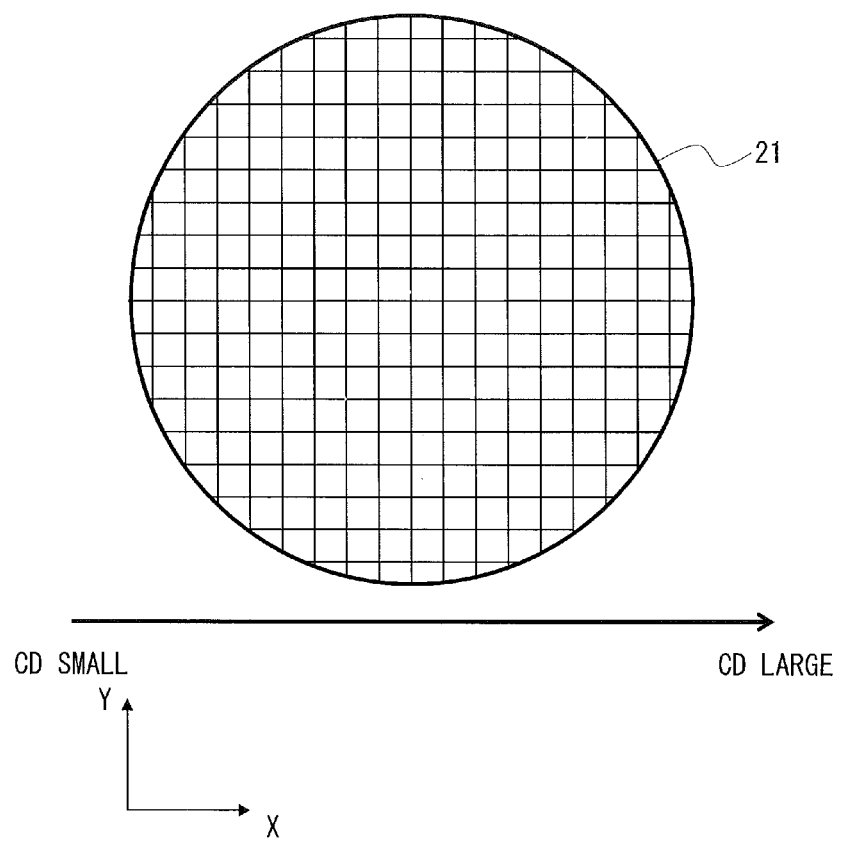
FIG. 3 schematically shows a semiconductor wafer, which is a reference sample.

For the parameter calculation performed by the parameter calculation unit 53, a statistical technique can be used. For example, as shown in FIG. 3, a reference sample 21 whose CD value changes according to the position in the X-direction is prepared. In the case of the reference sample 21 shown in FIG. 3, the CD value increases as the X-coordinate increases. Sample images of the reference sample 21 having such characteristics are obtained while changing the shooting condition. That is, a first reference sample image is taken under a first shooting condition and a second reference sample image is taken under a second shooting condition.

Figure 4:
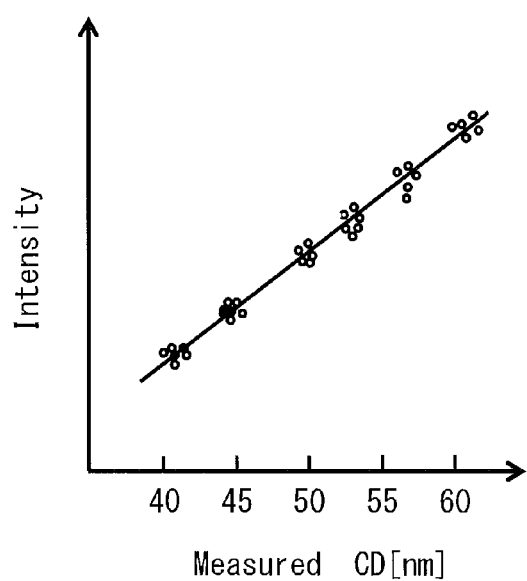
FIG. 4 shows a correlation between measured CD values and summation values of brightness values.

In addition to the acquisition of the reference sample images, the CD value of the reference sample is measured by using a measuring device different from the inspection apparatus. In this example, an actual CD value(s) is measured by CD-SEM (Scanning Electron Microscopy). Alternatively, an actual CD value(s) may be measured by OCD (Optical Critical Dimension) measurement. Then, a correlation between measured CD values and brightness values is obtained. For example, the parameter calculation unit 53 uses a multiple regression analysis as a statistical technique and thereby calculates the parameters (a1, a2 and b). The parameter calculation unit 53 performs a multiple regression analysis in which the brightness values of the first and second reference sample images are used as independent variables and the CD value is used as a dependent variable. By doing so, parameters (a1, a2 and b) that reduce the error can be calculated. In this way, the correlation between the CD values and the summation values can be obtained. The correlation between the measured CD values and the summation values is linear as shown in FIG. 4. Alternatively, the weighting variables may be set so that a curved distribution such as a quadratic function is obtained when the weighting function is obtained. In FIG. 4, the horizontal axis represents measured CD values and the vertical axis represents summation values.

Then, the parameter storage unit 54 stores the parameters (a1, a2 and b) calculated by the parameter calculation unit 53. Then, images of a sample 20, which is the object to be inspected, are taken under the same shooting conditions as those used when the parameters are determined. The inspection apparatus obtains a first sample image under the first shooting condition and a second sample image under the second shooting condition. Then, the brightness values of the first and second sample images are added up with weights by using the parameters (a1, a2 and b) in accordance with the above-shown Expression (1). In this way, the brightness values of the sample images can be converted into a CD value(s).

As described above, weighting parameters are calculated by using a statistical technique. That is, the parameters are calculated so that the error between the summation value obtained by the addition of the reference sample images with weights and the measured CD value is minimized. In this way, appropriate parameters can be set. Therefore, an inspection can be performed more accurately. Note that the measurement of the CD value may be performed by using a measuring device other than the CD-SEM. Alternatively, a reference sample whose CD value(s) is already known may be used.

In the above explanation, the sample images are obtained under the first and second shooting conditions. However, sample images may be obtained under three or more different shooting conditions. That is, brightness values of three or more sample images may be added up with weights. Even in this case, parameters can be set by a statistical technique using brightness values of reference sample images in a similar manner to that for the above-described example. Note that the number of weighting parameters increases according to the number of shooting conditions. For example, optimal weighting parameters can be calculated by performing a multiple regression analysis in which brightness values of reference sample images are used as independent variables. Then, the brightness values of the sample images are converted into a CD value(s) by using the calculated weighting parameters. By increasing the number of shooting conditions as described above, an inspection could be performed more accurately.

Further, reference sample images may be taken under three or more shooting conditions. Then, only some of these reference sample images may be used when parameters are set. For example, reference sample images may be obtained under three different shooting conditions, and then two of the three shooting conditions with which the error decreases may be selected. The inspection time can be reduced by reducing the number of shooting conditions. As a result, the throughput can be increased.

The above-described inspection method makes it possible to inspect a CD distribution with an accuracy of 1 nm or smaller. Note that although a CD (Critical Dimension) inspection is explained in the above-described examples, a film-thickness inspection can also be performed in a similar manner. Further, a taper angle inspection and a surface profile inspection can also be performed in a similar manner. For example, in the case of the film-thickness inspection, for the film-thickness, weighting parameters are set by using reference sample images taken under different shooting conditions as in the case of the CD value. The weighting parameters in the film-thickness inspection have values different from those of the weighting parameters in the CD inspection. Then, brightness values of sample images are added up with weights and an abnormality in the film-thickness can be determined based on the summation value. Further, the film-thickness inspection may use shooting conditions different from those for the CD inspection. In this way, the brightness values are converted to film-thicknesses by calculating the summation value of brightness values using the weighting parameters. As a result, the film-thickness can be accurately inspected. Further, different weighting parameters can be set for each of the CD, the film thickness, the taper angle, and the surface profile which are the size in the surface shape or the size in the height direction of a pattern. When at least one of the size in the surface shape or the size in the height direction of a pattern is the item to be inspected, shooting conditions having equivalent sensitivities for an item(s) other than the item to be inspected may be set.

In the above explanation, the present invention is applied to a CD inspection and a film-thickness inspection of a semiconductor wafer. However, inspections to which the present invention can be applied are not limited to these inspections. That is, an inspection to which the present invention is applied can be performed for any patterned substrates on which a pattern that is finer than the light-receiving pixels on the sample is formed. For example, the present invention can be applied to an inspection of a patterned substrate for a display panel such as a TFT substrate and an inspection of a photomask substrate. Further, in this exemplary embodiment, an inspection can be performed based on a correlation between brightness values of sample images and the size of the surface shape or the size in the height direction of a pattern of the sample. As a result, inspections of the surface shape of a pattern, surface roughness, a pattern width, a pattern interval, a taper angle, height information, a surface profile, and so on can be performed. Further, since images of a sample are taken at a low magnification, the whole sample can be inspected in a short time.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. An inspection apparatus for an object sample positioned on a support, the inspection apparatus comprising:
   a light source that illuminates the object sample on which a pattern is formed;
   a detector configured to detect light reflected from the object sample illuminated by the light source, the detector obtains a plurality of sample images by shooting the object sample under a plurality of shooting conditions for the object sample, each of the plurality of sample images corresponding to a respective shooting condition and in each sample image a position on a surface of the object sample is associated with a brightness value; and
   a processing device configured to perform an inspection of the object sample based on a correlation between a reference brightness value of each of a plurality of reference images obtained by the detector and at least one of a dimension value of a surface in a height direction or an in-plane direction of a reference sample, wherein the processing device is configured to perform the inspection by (1) for each sample image determining a respective product of a brightness value of the sample image and a weighted parameter corresponding to the respective shooting condition of the sample image, (2) determining a sum of the respective products, and (3) comparing the sum to a threshold, each of the weighted parameters being based on a determined reference brightness value for the reference sample observed under the respective shooting condition associated with the weighted parameter.

2. The inspection apparatus according to claim 1, wherein the weighted parameters are calculated based on a measured value of the size obtained by measuring the reference sample and the reference brightness value of the reference image of the reference sample by using a statistical technique.

3. The inspection apparatus according to claim 2, wherein a multiple regression analysis is used as the statistical technique.

4. The inspection apparatus according to claim 1, wherein the shooting condition is changed by changing at least one of a wavelength of illumination light, polarization of the illumination light, an illuminating angle of the illumination light, a shape of the illumination light, a detecting angle of the detector, and an angle of the sample.

5. The inspection apparatus according to claim 1, wherein at least one of the dimension value in a surface shape and the dimension value in the height direction of a pattern of the object sample is an item to be inspected, shooting conditions whose sensitivities for an item other than the item to be inspected are equivalent to each other are set.

6. The inspection apparatus according to claim 1, wherein the object sample is a semiconductor wafer, a TFT substrate, or a photomask, and
   a CD of the pattern, a film thickness, a taper angle, or a surface profile is inspected.

7. The inspecting apparatus according to claim 1, wherein the brightness value is obtained for each pixel or each area of the object sample, wherein each area includes a plurality of the pixels.

8. An inspection method comprising:
   illuminating an object sample on which a pattern is formed;
   detecting, by a detector, light reflected from the illuminated object sample to take a plurality of sample images by shooting the object sample under a plurality of shooting conditions for the object sample, each of the plurality of sample images corresponding to a respective shooting condition in which a position on a surface of the object sample is associated with a brightness value;
   performing an inspection of the object sample based on a correlation between a reference brightness value of each of a plurality of reference images obtained by the detector and at least one of a dimension value of a surface in a height direction or an in-plane direction of a reference sample;
   determining a respective product of a brightness value of the sample image and a weighted parameter corresponding to the respective shooting condition of the sample image;
   determining a sum of the respective products; and
   comparing the sum to a threshold, each of the weighted parameters being based on a determined reference brightness value for the reference sample observed under the respective shooting condition associated with the weighted parameter.

9. The inspection method according to claim 8, wherein the weighted parameters are calculated based on a measured value of the size obtained by measuring the reference sample and the reference brightness value of the reference image of the reference sample by using a statistical technique.

10. The inspection method according to claim 9, wherein a multiple regression analysis is used as the statistical technique.

11. The inspection method according to claim 8, wherein the shooting condition is changed by changing at least one of a wavelength of illumination light, polarization of the illumination light, an illuminating angle of the illumination light, a shape of the illumination light, a detecting angle of the detector, and an angle of the sample.

12. The inspection method according to claim 8, wherein at least one of the dimensional value in a surface shape and the dimensional value in the height direction of a pattern of the object sample is an item to be inspected, shooting conditions whose sensitivities for an item other than the item to be inspected are equivalent to each other are set.

13. The inspection method according to claim 8, wherein the sample is a semiconductor wafer, a TFT substrate, or a photomask, and
   a CD of the pattern, a film thickness, a taper angle, or a surface profile is inspected.

14. The inspecting method according to claim 8, wherein the brightness value is obtained for each pixel or each area of the object sample, wherein each area includes a plurality of the pixels.

* * * * *